(12) United States Patent
KenKnight et al.

(10) Patent No.: US 6,939,345 B2
(45) Date of Patent: *Sep. 6, 2005

(54) METHOD FOR REDUCING RESTENOSIS IN THE PRESENCE OF AN INTRAVASCULAR STENT

(75) Inventors: Bruce H. KenKnight, Maple Grove, MN (US); Jay A. Warren, North Oaks, MN (US); Stephen John Hahn, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/397,623

(22) Filed: Mar. 26, 2003

(65) Prior Publication Data

US 2003/0187340 A1 Oct. 2, 2003

Related U.S. Application Data

(63) Continuation of application No. 09/940,337, filed on Aug. 27, 2001, now Pat. No. 6,648,881, which is a continuation of application No. 09/294,724, filed on Apr. 19, 1999, now Pat. No. 6,317,615.

(51) Int. Cl.[7] .............................................. A61B 18/04
(52) U.S. Cl. ........................... 606/32; 606/41; 606/194; 606/198; 600/372; 600/381
(58) Field of Search ................. 606/32, 34, 41–50, 606/192, 194, 196, 198; 600/372, 381

(56) References Cited

U.S. PATENT DOCUMENTS

| | | | |
|---|---|---|---|
| 4,800,882 A | 1/1989 | Gianturco | 128/343 |
| 4,907,336 A | 3/1990 | Gianturco | 29/515 |
| 4,936,281 A | 6/1990 | Stasz | 128/660.03 |

(Continued)

FOREIGN PATENT DOCUMENTS

| | | | | |
|---|---|---|---|---|
| WO | WO-98/56324 | 12/1998 | | A61F/7/12 |
| WO | WO-99/42176 | 8/1999 | | A61N/5/00 |

OTHER PUBLICATIONS

Burns, Brent E., "Fabrication Technology for a Chronic In–Vivo Pressure Sensor" *1984 International Electron Devices Meeting Technical Digest*, (1984), 210–212.

Carr, William N., "Integrated Pressure Sensor With Remote Power Source and Remote Readout", *The 8th International Conference on Solid–State Sensors and Actuators and Eurosensors IX, Digest of Technical Papers, Stockholm, Sweden*, Jun. 25–29, 1995), 624–627.

(Continued)

*Primary Examiner*—Lee S. Cohen
(74) *Attorney, Agent, or Firm*—Schwegman, Lundberg, Woessner & Kluth, P.A.

(57) ABSTRACT

A first electrode is positioned within an artery proximate an implanted intravascular stent. A second electrode is positioned at a separate location relative the position of the first electrode. Electrical energy is then delivered between the first and the second electrodes to produce an electrical field adjacent the implanted intravascular stent. When a intravascular stent is implanted in a coronary artery, the delivery of the electrical energy is coordinated to cardiac cycles detected in sensed cardiac signals, where the delivery of the electrical energy between the first electrode and the second electrode occurs during a predetermined portion of the cardiac cycle.

76 Claims, 7 Drawing Sheets

U.S. PATENT DOCUMENTS

| | | | |
|---|---|---|---|
| 4,990,155 A | 2/1991 | Wilkoff | 606/191 |
| 4,994,033 A | 2/1991 | Shockey et al. | 604/101 |
| 5,041,126 A | 8/1991 | Gianturco | 606/195 |
| 5,078,736 A | 1/1992 | Behl | 623/1 |
| 5,108,417 A | 4/1992 | Sawyer | 606/198 |
| 5,178,618 A | 1/1993 | Kandarpa | 606/28 |
| 5,292,321 A | 3/1994 | Lee | 606/28 |
| 5,314,444 A | 5/1994 | Gianturco | 606/195 |
| 5,344,425 A | 9/1994 | Sawyer | 606/198 |
| 5,474,563 A | 12/1995 | Myler et al. | 606/108 |
| 5,607,463 A | 3/1997 | Schwartz et al. | |
| 5,637,113 A | 6/1997 | Tartaglia et al. | 623/1 |
| 5,658,281 A | 8/1997 | Heard | 606/48 |
| 5,665,103 A | 9/1997 | Lafontaine et al. | 606/192 |
| 5,669,924 A | 9/1997 | Shaknovich | 606/108 |
| 5,693,085 A | 12/1997 | Buirge et al. | 623/1 |
| 5,697,380 A | 12/1997 | Quiachon et al. | 128/772 |
| 5,700,286 A | 12/1997 | Tartaglia et al. | 623/1 |
| 5,733,302 A | 3/1998 | Myler et al. | 606/195 |
| 5,746,691 A | 5/1998 | Frantzen | 600/36 |
| 5,749,890 A | 5/1998 | Shaknovich | 606/198 |
| 5,749,914 A | 5/1998 | Janssen | 607/116 |
| 5,766,192 A | 6/1998 | Zacca | 606/159 |
| 5,775,338 A | 7/1998 | Hastings | 128/898 |
| 5,807,398 A | 9/1998 | Shaknovich | 606/108 |
| 5,814,089 A | 9/1998 | Stokes et al. | |
| 5,827,322 A | 10/1998 | Williams | 606/198 |
| 5,843,117 A | 12/1998 | Alt et al. | 606/194 |
| 5,846,218 A | 12/1998 | Brisken et al. | 604/22 |
| 5,876,433 A | 3/1999 | Lunn | 623/1 |
| 5,876,445 A | 3/1999 | Andersen et al. | 623/11 |
| 5,882,329 A | 3/1999 | Patterson et al. | 604/49 |
| 5,895,406 A | 4/1999 | Gray et al. | 606/198 |
| 5,899,917 A | 5/1999 | Edwards et al. | 606/195 |
| 5,902,263 A | 5/1999 | Patterson et al. | 604/22 |
| 5,906,636 A | 5/1999 | Casscells, III et al. | 607/96 |
| 5,913,871 A | 6/1999 | Werneth et al. | 606/194 |
| 5,921,954 A * | 7/1999 | Mohr et al. | 604/508 |
| 5,922,021 A | 7/1999 | Jang | 623/1 |
| 5,935,162 A | 8/1999 | Dang | 623/1 |
| 5,938,623 A | 8/1999 | Quiachon et al. | 600/585 |
| 5,938,682 A | 8/1999 | Hojeibane et al. | 606/198 |
| 5,941,869 A | 8/1999 | Patterson et al. | 604/508 |
| 5,941,895 A | 8/1999 | Myler et al. | 606/195 |
| 5,944,710 A | 8/1999 | Dev et al. | 604/500 |
| 5,948,016 A | 9/1999 | Jang | 623/1 |
| 5,954,743 A | 9/1999 | Jang | 606/198 |
| 5,954,761 A | 9/1999 | Macheck et al. | 607/126 |
| 5,957,929 A | 9/1999 | Brenneman | 606/108 |
| 5,967,984 A | 10/1999 | Chu et al. | 600/439 |
| 5,967,986 A | 10/1999 | Cimochowski et al. | 600/454 |
| 5,972,029 A | 10/1999 | Fuisz | 623/1 |
| 5,977,163 A | 11/1999 | Li et al. | 514/449 |
| 5,980,551 A | 11/1999 | Summers et al. | 606/194 |
| 5,980,563 A * | 11/1999 | Tu et al. | 607/113 |
| 5,980,566 A | 11/1999 | Alt et al. | |
| 6,053,913 A | 4/2000 | Tu et al. | 606/41 |
| 6,102,908 A | 8/2000 | Tu et al. | 606/194 |
| 6,129,725 A * | 10/2000 | Tu et al. | 606/41 |
| 6,141,588 A | 10/2000 | Cox et al. | |
| 6,179,824 B1 | 1/2001 | Eggers et al. | 604/500 |
| 6,272,377 B1 | 8/2001 | Sweeney et al. | |
| 6,317,615 B1 | 11/2001 | KenKnight et al. | |
| 6,442,413 B1 | 8/2002 | Silver | |
| 6,519,488 B2 | 2/2003 | KenKnight et al. | 600/372 |
| 6,582,423 B1 * | 6/2003 | Thapliyal et al. | 606/41 |
| 6,645,145 B1 | 11/2003 | Dreschel et al. | |
| 6,648,881 B2 * | 11/2003 | KenKnight et al. | 606/41 |
| 2002/0026228 A1 | 2/2002 | Schauerte | |
| 2003/0069606 A1 | 4/2003 | Girouard et al. | |
| 2003/0153952 A1 | 8/2003 | Auricchio et al. | |
| 2003/0158584 A1 | 8/2003 | Cates et al. | |
| 2004/0093034 A1 | 5/2004 | Girouard et al. | |

OTHER PUBLICATIONS

Chau, Hin–Leung, "An Ultraminiature Solid–State Pressure Sensor for a Cardiovascular Catheter", *IEEE Transactions on Electron Devices*, (Dec. 1988), 2355–2362.

Pastore, Joseph M., "Method And Apparatus For Modulating Cellular Metabolism During Post–Ischemia Or Heart Failure", *Application Ser. No. 10/645,823, Filed Aug. 21, 2003 Attorney Docket No. 279.606US1*, 46 pages.

Spiegel, Egbert, "A CMOS Sensor and Signal Conversion Chip for Monitoring Arterial Blood Pressure and Temperature", *IEEE International Solid–State Circuits Conference*, (Feb, 20, 1992), 126–127.

Ziaie, Babak, "A Single–Channel Implantable Microstimulator for Functional Neuromuscular Stimulation", *IEEE Transactions on Biomedical Engineering, 44*, (Oct. 1997), 909–920.

* cited by examiner

METHOD FOR REDUCING RESTENOSIS IN THE PRESENCE OF AN INTRAVASCULAR STENT

CROSS-REFERENCE TO RELATED APPLICATION(S)

This application is a continuation of U.S. patent application Ser. No. 09/940,337, filed on Aug. 27, 2001 now U.S. Pat. No. 6,648,881, which is a continuation of U.S. patent application Ser. No. 09/294,724, filed on Apr. 19, 1999, now issued as U.S. Pat. No. 6,317,615, the specifications of which are incorporated herein by reference.

FIELD OF THE INVENTION

The present subject matter relates generally to medical devices and more particularly to a method and system for producing an electric field adjacent an intravascular stent.

BACKGROUND OF THE ART

The normal human heart is a strong, muscular pump a little larger than a fist. It pumps blood continuously through the circulatory system. Each day the average heart "beats" (or expands and contracts) 100,000 times and pumps about 2,000 gallons of blood. In a 70-year lifetime, an average human heart beats more than 2.5 billion times.

The heart pumps blood through a circulatory system, which is a network of elastic tubes through which blood flows as it carries oxygen and nutrients to all parts of the body. The circulatory system includes the heart, lungs, arteries, arterioles (small arteries), and capillaries (minute blood vessels). It also includes venules (small veins) and veins, the blood vessels through which blood flows as it returns to the heart.

The circulating blood brings oxygen and nutrients to all the organs and tissues of the body, including the heart itself. The blood also picks up waste products from the body's cells. These waste products are removed as they're filtered through the kidneys, liver and lungs.

Over time, the coronary arteries which supply the heart muscle with blood can become clogged. One cause of clogged arteries is due to a condition called atherosclerosis, or hardening of the arteries. Atherosclerosis causes a constriction of the inner lumen of the affected artery when the lumen of the arteries become more narrow due to a pathological accumulation of cells, fats and cholesterol called plaque. The descriptive term given to this narrowing of the coronary arteries is "stenosis." Stenosis means constriction or narrowing. A coronary artery that is constricted or narrowed is referred to as stenosed. When stenosis of the coronary artery is sufficient to deprive the heart muscle of the oxygen levels necessary for cell viability, the result is typically myocardial infarction, typically referred to as a heart attack.

A heart attack occurs when the blood supply to part of the heart muscle itself, the myocardium, ceases or is severely reduced. This occurs when one or more of the arteries supplying blood to the heart muscle (coronary arteries) becomes partially or completely obstructed by plaque stenoses. If cessation of the blood supply occurs for a long time, heart muscle cells suffer irreversible injury and die. Severe disability or death can result, depending on how much heart muscle is damaged.

Coronary artery bypass surgery is a heart operation used to treat coronary artery disease. In coronary artery bypass surgery a blood vessel is used to go around or "bypass" clogged coronary (heart) arteries. During the "bypass" procedure, a blood vessel from the patient's chest or leg is used as the "bypass" conduit. For venous "bypass" grafts, one end of the vessel is attached to the aorta (the large artery coming out of the heart) and the other end is attached to the coronary artery below the point where it's clogged. Once the clog has been bypassed, blood can once again flow through the bypass graft to the heart, in a manner that prevents ischemia and infarction. Almost half a million coronary bypass operations are performed each year in the USA.

Another procedure for opening clogged coronary arteries is to perform percutaneous transluminal coronary angioplasty, or balloon angioplasty. Balloon angioplasty is an established and effective therapy for some patients with coronary artery disease. Balloon angioplasty is used to dilate (widen) arteries narrowed by plaque. During the procedure, a catheter with a deflated balloon on its tip is passed into the narrowed part of the artery. The balloon in then inflated, and the narrowed area is widened. Balloon angioplasty is a less traumatic and less expensive alternative to bypass surgery for some patients with coronary artery disease. However, in 25 to 30 percent of patients the dilated segment of the artery renarrows (restenosis) within six months after the procedure. The patient may then require either to repeat the balloon angioplasty or to undergo coronary bypass surgery.

One approach to preventing restenosis has been to insert a "stent" across the stenosed area of coronary artery. A stent is a metallic wire mesh tube that is used to prop open an artery that has been recently dilated using balloon angioplasty. The stent is collapsed to a small diameter, placed over an angioplasty balloon catheter and moved into the area of the blockage. When the balloon is inflated, the stent expands, locking in place to form a rigid support (structural scaffolding) which holds the artery lumen open. The stent remains in the artery permanently to help improve blood flow to the heart muscle. However, reclosure (restenosis) remains an important issue with the stent procedure.

Several approaches have been taken to reduce the occurrence of restenosis associated with the stent procedure. Stents have been impregnated with drugs and chemicals that emit radiation (gamma-rays) in an attempt to reduce the frequency of restenosis. Also, drug eluting stents have been used in an attempt to reduce the occurrence of restenosis. However, a need still exists for additional safe and effective treatments to prevent restenosis after the placement of an intravascular stent.

SUMMARY OF THE INVENTION

The present subject matter provides a method and a system for producing electrical energy adjacent an intravascular stent. The electrical energy (or current density) supplied to the artery surrounding the stent is sufficient to structurally modify, damage and/or kill cells within the artery. By effecting the cells of the artery surrounding the stent, it is believed that the occurrence of restenosis associated with the stent procedure will be reduced.

The present subject matter includes a system and method for positioning a first electrode within the vasculature proximate an implanted stent, where the stent is electrically conductive. A second electrode is then positioned at a remote position relative to the first electrode. In one embodiment, the remote position is on the dermal surface of the patient. Cardiac signals are then sensed from the patient. The cardiac signals include cardiac cycles which indicate the electrical events of cardiac excitation. Electrical energy is then delivered between the first electrode and the second electrode during a predetermined portion of a sensed cardiac cycle.

In one embodiment, the first electrode is positioned on a transvenous catheter. The transvenous catheter includes a first lead conductor which is contained within the elongate body of the transvenous catheter and serves to couple the first electrode to the first lead connector. In an additional embodiment, the second electrode is coupled to an external lead. The external lead includes an elongate body and a second lead conductor contained within the elongate body that couples the second electrode to a second lead connector.

The transvenous catheter allows at least a portion of the first electrode to be positioned within the lumen of the implanted stent. Alternatively, the first electrode is positioned entirely within the lumen of the implanted stent. In one embodiment, first electrode is positioned within the lumen of the stent in such a manner that the first and second electrode ends of the first electrode align with the first and second stent ends of the implanted stent, respectively. In one embodiment, the length of the first electrode is between 80 and 120% of the predetermined length of the intravascular stent.

In one embodiment, the first and second electrodes are coupled to a pulse generator. In one embodiment, the pulse generator includes a programming circuit coupled to a display screen, where the programming circuit is used to control the display screen to request parameter values for the electrical energy pulse. The pulse generator further includes a data input device which is coupled to the programming circuit and the display screen. The programming circuit can then receive parameter values for the electrical pulses through the data input device. In one embodiment, the data input device is an alphanumeric keyboard.

In one embodiment, the first and second electrodes are releasably coupled to the pulse generator through a first input/output socket and a second input/output socket, respectively. In one embodiment, cardiac signals are sensed between the first and second electrodes and the cardiac signals are provided to an electrogram analysis circuit. In one embodiment, the electrogram analysis circuit detects cardiac complexes in the sensed cardiac signal. A microprocessor is additionally coupled to the programming circuit, the electrogram analysis circuit and an energy source. The microprocessor receives the parameter values from the programming circuit and the cardiac complexes in the sensed cardiac signal from the electrogram analysis circuit. The microprocessor also controls the energy source to generate the electrical energy pulse having the parameter values for the intravascular stent when a predetermined portion of a cardiac complex occurs in the cardiac signal.

In an additional embodiment, two or more surface electrocardiogram electrodes are coupled to the pulse generator. The electrogram analysis circuit is adapted to receive one or more cardiac signals (including cardiac complexes) sensed between the two or more surface electrocardiogram electrodes. The microprocessor then controls the energy source to generate the electrical energy pulse having the parameter values for the intravascular stent when a predetermined portion of a cardiac complex occurs in the cardiac signal sensed between the two or more surface electrocardiogram electrodes.

DETAILED DESCRIPTION

Figure 1:
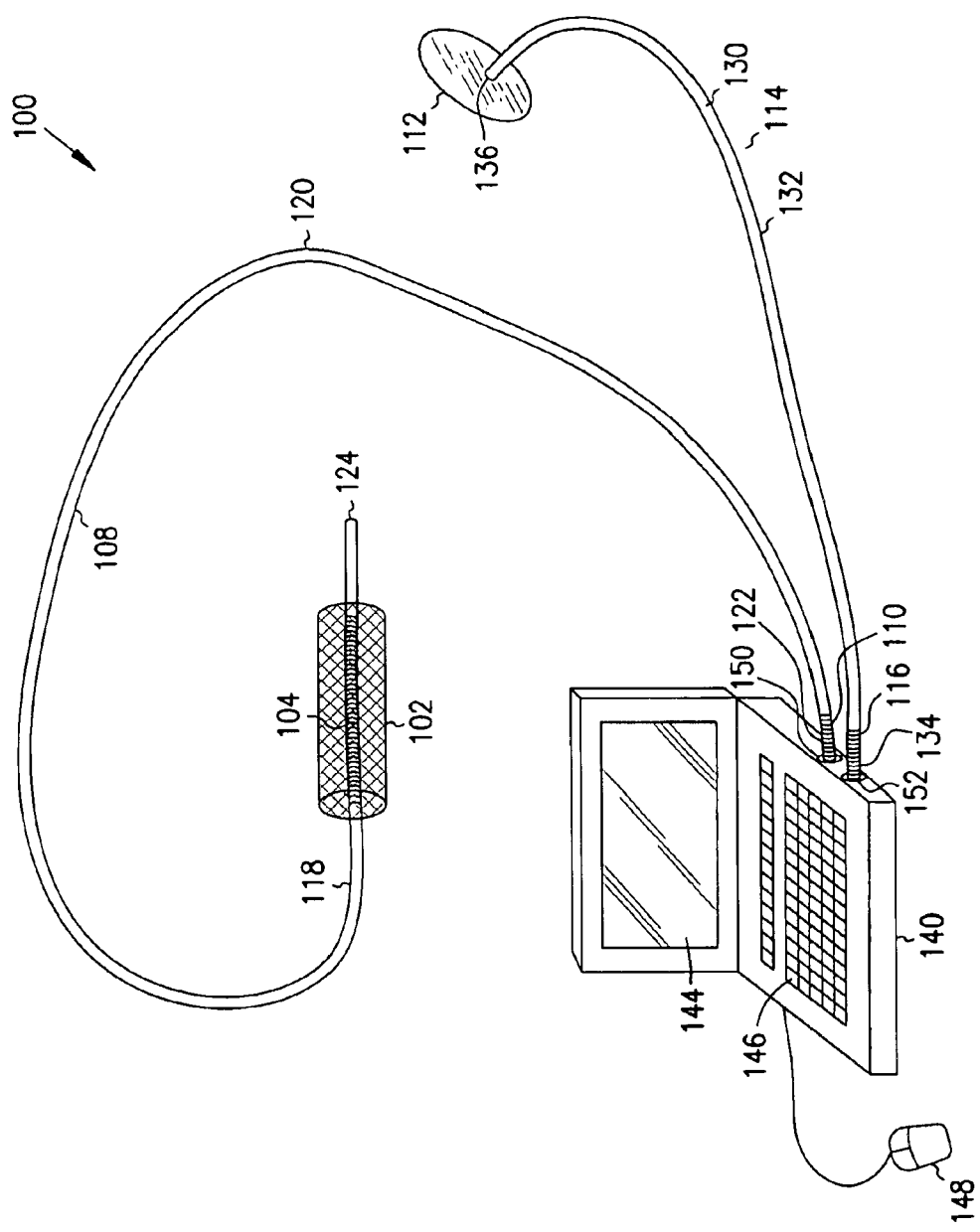
FIG. 1 is a schematic of a system according to one embodiment of the present subject matter.

In the following detailed description, reference is made to the accompanying drawings which form a part hereof and in which is shown by way of illustration specific embodiments in which the invention can be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

Restenosis of arteries after balloon angioplasty continues to be a serious problem. Restenosis has even been found to be a problem after the placement of an intravascular stent which is designed to hold an artery open after balloon angioplasty. The present subject matter addresses the problem of restenosis associated with the stent procedure by providing electrical energy to the artery tissues surrounding the stent. The electrical energy (or current density) supplied to the artery surrounding a stent is sufficient to structurally modify, damage and/or kill cells within the artery.

The general structure of an artery has three layers. The first layer consists of a single continuous layer of endothelial cells along the lumen of the artery. The endothelial cells attach to a second layer, which is a muscular middle layer. This second layer is referred to as the tunica media. The muscular middle layer consists principally of muscular tissue (smooth muscle cells) which are arranged in lamellae and disposed circularly around the vessel. The thickness of the artery wall is due in large part to this muscular middle layer. The third layer is the outer most layer and is referred to as the tunica adventitia. The third layer consists mainly of fine and closely felted bundles of connective tissue and elastic fibers.

An electrical field is localized to the arterial tissue surrounding the stent. In one embodiment, the electrical field is produced in tissues adjacent to the stented region of an artery by effecting a voltage difference between a first electrode positioned adjacent the stent and a second electrode positioned at a remote position relative to the first electrode. The electrical energy is supplied from a capacitor which creates a potential difference (voltage) between the first electrode and the second electrode. The potential difference results in creation of an electric field having a space-varying and time-varying intensity that can be expressed as current density. In one embodiment, the strength of the electrical energy is sufficient to irreparably damage the cells within the structure of the artery, where the cells most heavily damaged are the smooth muscle cells located in the medial layer of the artery. However, the electrical energy is not sufficiently strong to cause significant modification of adjacent myocardial tissue, thereby leaving the remaining cardiac tissue unaffected by the electrical energy.

Referring now to FIG. 1, there is shown a system 100 according to one embodiment of the present subject matter. The system 100 an intravascular stent 102, where the intravascular stent 102 in one embodiment is made of metal. The system 100 further includes a first electrode 104, where the first electrode 104 is positioned on a catheter 108 and is coupled to a first lead connector 110 through a first lead conductor (not shown). Additionally, the system 100 includes a second electrode 112, the second electrode 112 positioned on an external lead 114 and is coupled to a second lead connector 116 through a second lead conductor (not shown).

The catheter 108 includes an elongate body 118 having a peripheral surface 120, a proximal end 122, and a distal end 124. The first electrode 104 is positioned on the peripheral surface 120 of the catheter 108 between the proximal end 122 and the distal end 124. A first lead conductor (not shown) is contained within the elongate body 118 and couples the first electrode 104 to the first lead connector 110 and the proximal end 122. The catheter 108 further includes a guidewire lumen (not shown) which extends through at least a portion of the elongate body 118. In an alternative embodiment, the elongate body 118 is adapted to allow the guidewire to extend through the entire length of the elongate body 118.

The external lead 114 includes an elongate body 130 having a peripheral surface 132, a proximal end 134, and a distal end 136. The second electrode 112 is positioned, or attached, at the distal end 136 of the external lead 114. A second lead conductor (not shown) is contained within the elongate body 130 and couples the second electrode 112 to the second lead connector 116 at the proximal end 134 of the elongate body 130. In one embodiment, the second electrode 112 is a patch electrode which is constructed of a conductive gel overlying a metallic foil, as are known.

The system 100 further includes a pulse generator 140. The pulse generator 140 includes a programming circuit (not shown) and a display screen 144. The programming circuit is coupled to and controls the display screen 144 to request values for an electrical pulse to be entered into the pulse generator 140. A data input device is coupled to the programming circuit and display screen 144. The data input device receives the parameter values for the electrical pulse and displays the values on the display screen 144. In one embodiment, the data input device is a keyboard 146. Alternatively, the data input device is a touch sensitive layer (not shown) integrated into the display screen 144 which allow for data input by touching predetermined regions of the layer. Additionally, a computer mouse 148 can be used to supply parameter values, along with other information, by responding to and inputting information presented on the display screen 144.

The pulse generator 140 further includes a first input/output socket 150 and a second input/output socket 152. The first and second input/output sockets 150 and 152 are coupled to an electrogram analysis circuit (not shown) housed within the pulse generator 140. The first lead connector 110 and the second lead connector 116 releasably couple to the first and second input/output sockets 150 and 152, which allows for electrical signals to be sensed between the first and second electrodes, 104 and 112. In one embodiment, the electrogram analysis circuit includes signal amplifiers to amplify the electrical signals sensed between the first and second electrodes 104 and 112.

In one embodiment, the electrical signals sensed between the first and second electrodes 104 and 112 are cardiac signals. The electrogram analysis circuit receives the sensed cardiac signals and analyzes the cardiac signal to detect the occurrence of cardiac complexes in the sensed cardiac signal. In one embodiment, the electrogram analysis circuit detects the occurrence of the QRS-complex of the cardiac complex. Alternatively, the electrogram analysis circuit detects other known portions of the cardiac complex, such as the occurrence of T-waves or the occurrence of the complete cardiac complex.

The pulse generator 140 further includes a microprocessor coupled to the programming circuit, the electrogram analysis circuit and an electrical energy source (not shown). The microprocessor receives the parameter values for the electrical pulse from the programming circuit. Cardiac complexes in the sensed cardiac signal are also provided to the microprocessor from the electrogram analysis circuit. The microprocessor then uses this information to control an energy source to produce the electrical energy pulse having the parameter values when a predetermined portion of a cardiac complex occurs in the cardiac signal. In one embodiment, the microprocessor controls the energy source to generate the electrical energy pulse for the intravascular stent when the predetermined portion of a cardiac complex occurs in the cardiac signal.

In one embodiment, the energy source supplies electrical energy and is coupled to a transducer which converts electrical energy to radio frequency energy. Radio frequency energy is then produced and can be subsequently delivered to the intravascular stent when the predetermined portion of a cardiac complex occurs in the cardiac signal. In an alternative embodiment, the energy source supplies electrical energy to one or more electrical capacitors operatively coupled to the energy source, microprocessor and the first and second input/output sockets 150 and 152. Upon charging the electrical capacitors to a sufficient energy level, the microcontroller controls the discharge of the electrical capacitors to produce an electrical energy pulse for the intravascular stent.

In one embodiment, the present subject matter is used to deliver electrical energy to an intravascular stent implanted in an artery. Procedures and locations for implanting intravascular stent are known in the art. Once a stent has been implanted in an artery, the cardiac cells adjacent the intravascular stent are altered by providing electrical energy in the region surrounding the stent. In one embodiment, the electrical energy is provided to the region surrounding the stent by discharging electrical energy between the first electrode and the second electrode, where the first electrode is positioned within the artery proximate the implanted stent and the second electrode is positioned at a location that is set apart, or remote, from the first electrode to permit electrical energy to be delivered between the first and second electrodes during a predetermined portion of the cardiac cycle.

In one embodiment, cardiac complexes are sensed by the pulse generator 140 using the first electrode 104 and the second electrode 112. The sensed cardiac complexes are then used to coordinate the production of the electrical energy for the stent 102. In one embodiment, the electrogram signals are used by the pulse generator 140 to deliver the electrical energy during the predetermined portion of the sensed cardiac complexes. For example, electrical energy is coordinated to occur during a sensed QRS-complex of the cardiac cycle. Alternatively, the electrical energy is delivered outside the occurrence of the T-wave of the cardiac cycle in a manner that avoids creation of cardiac arrhythmias.

Figure 2:
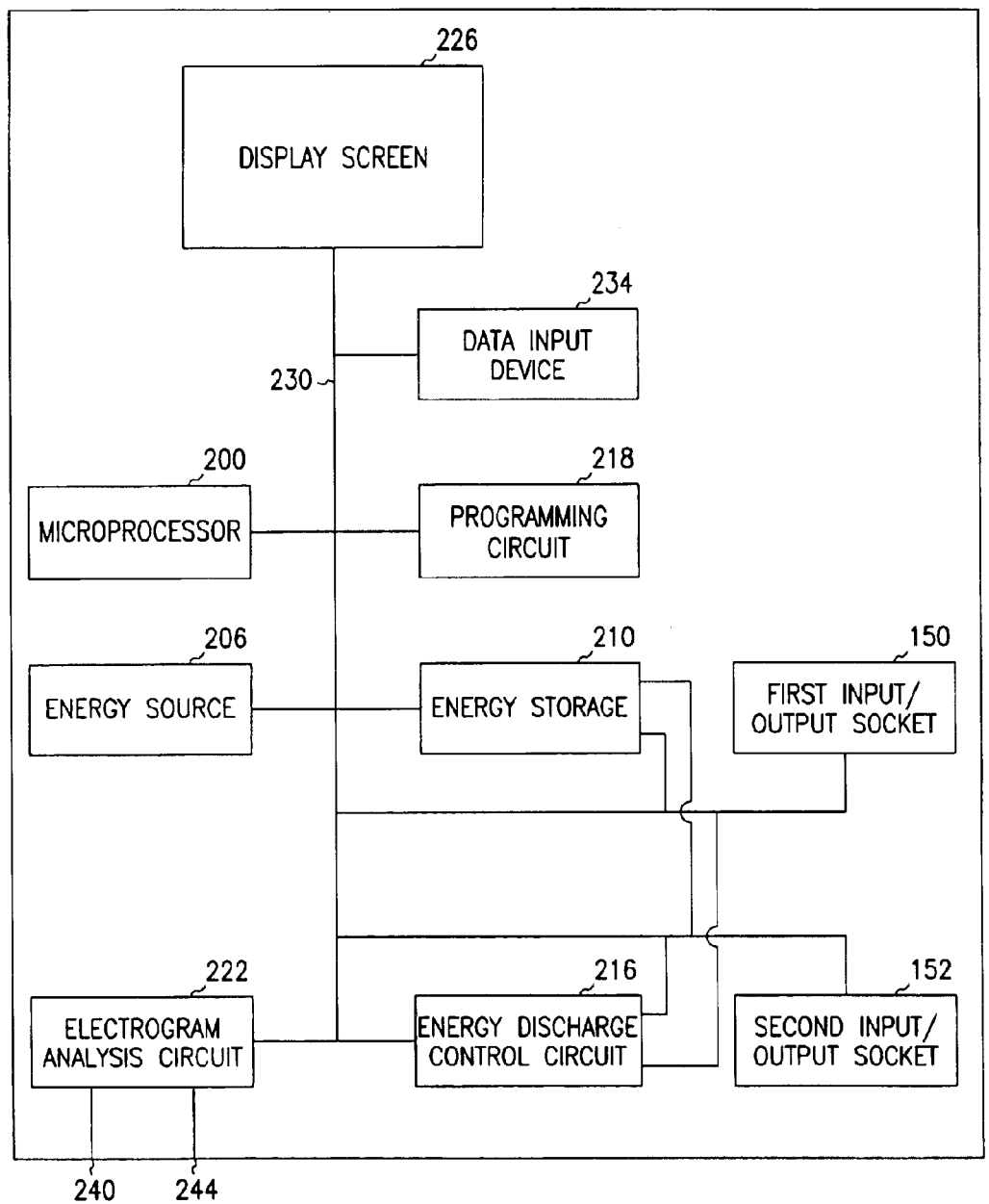
FIG. 2 is a block diagram of a pulse generator according to one embodiment of the present subject matter.

Referring now to FIG. 2, there is shown a block diagram of one embodiment of the pulse generator 140. In one embodiment, the pulse generator 140 is a programmable microprocessor based pulse generator. The pulse generator 140 includes a microprocessor 200, an energy source 206, energy storage 210, an energy discharge control circuit 216, a programming circuit 218, an electrogram analysis circuit 222, and a display screen 226, wherein the components are electrically connected by bus 230.

The display screen 226 is coupled to the programming circuit 218 by bus 230. In one embodiment, the programming circuit 218 prompts a user through the display screen 226 to input parameters values for the electrical energy pulses to be produced by the pulse generator 140. Parameter values programmable in the pulse generator 140 include, but are not limited to, energy level, voltage, current, number of pulses or shocks to be produced, and duration of each pulse.

Information related to the operation of the electric pulse generator 140 is displayed on the display screen 226. In one embodiment, parameter values and operational commands for the pulse generator 140 are entered through a data input device 234. In one embodiment, the data input device is a keyboard as shown in FIG. 1. The data input device 234 is interactively coupled to the programming circuit 218. Alternatively, the parameter values are provided through the interactive display screen 226, where the display screen 226 has touch sensitive screen to allow parameter values to be entered by touching the display screen 226.

In addition to having parameter values entered into the programming circuit 218, the pulse generator 140 can be used to calculate impedance values for cardiac tissue region surrounding an implanted stent. In one embodiment, the impedance measurements are used to calculate appropriate voltage values for electrical energy pulses generated by the pulse generator 140. In one embodiment, the impedance is determined by producing and delivering a constant current of insufficient magnitude to effect heart contraction from the energy source 206 under the control of the energy discharge control circuit 216 to the first electrode and the second electrode. Alternatively, an alternating current is supplied by the energy source 206 under the control of the energy discharge control circuit 216 to the first electrode and the second electrode.

As the constant current is being delivered across the first and second electrodes, the voltage resulting from the delivered current in sensed by the electrodes. From the measured resultant voltage the microprocessor 200 calculates the impedance of the tissue through which the electrical current passed. The impedance value is then used to calculate a voltage for the electrical energy to be produced by the pulse generator 140. In one embodiment, the electrical energy can then be delivered to the stented region of the artery.

In one embodiment, the first lead connector 110 of the catheter 108 and the second lead connector 116 of the external lead 114 are physically and electrically coupled to the pulse generator 140 through the first input/output socket 150 and the second input/output socket 152. In one embodiment, the polarity of electrical energy delivered to the first input/output socket 150 and a second input/output socket 152 is controlled by energy discharge control circuit 216. In an alternative embodiment, the polarity of the first and second input/output sockets 150 and 152 are fixed as either the cathode terminal or the anode terminal.

The pulse generator 140 further includes the electrogram analysis circuit 222. In one embodiment, the electrogram analysis circuit 222 analyzes one or more sensed electrocardiogram signals. In one embodiment, an electrocardiogram signal is sensed between the first electrode 104 and the second electrode 112. In an alternative embodiment, an electrocardiogram signal is sensed between two or more surface electrodes, where the cardiac signals are provided to the pulse generator 140 through electrocardiogram input sockets 240 and 244 positioned on the pulse generator 140 and electrically coupled to the electrogram analysis circuit 222.

As the electrocardiogram signal is sensed, the electrogram analysis circuit 222 detects the occurrence of QRS-complexes in the signal. The energy discharge control circuit 216 operates to cause the energy source 206 and/or the energy storage 210 to produce electrical energy during the occurrence of QRS-complexes. Alternatively, the electrogram analysis circuit 222 detects the occurrence of both QRS-complexes and T-waves in the sensed cardiac signal. The energy discharge control circuit 216 is then used to ensure the electrical energy is not produced, and then subsequently delivered, during the occurrence of a T-wave.

In one embodiment, when the pulse generator 140 produces the electrical energy, the microprocessor 200 commands the energy source 206 to begin charging energy storage 210. In one embodiment, the energy storage 210 is one or more capacitors as are known in the art. When the energy source 210 has charged to a sufficient energy level, the energy discharge control circuit 216 is used to produce one or more pulses of electrical energy. In one embodiment, the one or more pulses of electrical energy can then be delivered to the first and second input/output sockets 150 and 152 according to the parameter values programmed into the pulse generator 140.

In an alternative embodiment, the pulse generator 140 further includes a transducer (not shown), where the energy source 206 supplies electrical energy and is coupled to the transducer which converts electrical energy to radio frequency energy. The radio frequency energy pulses are then produced by the pulse generator 140 for the intravascular stent.

Figure 3:
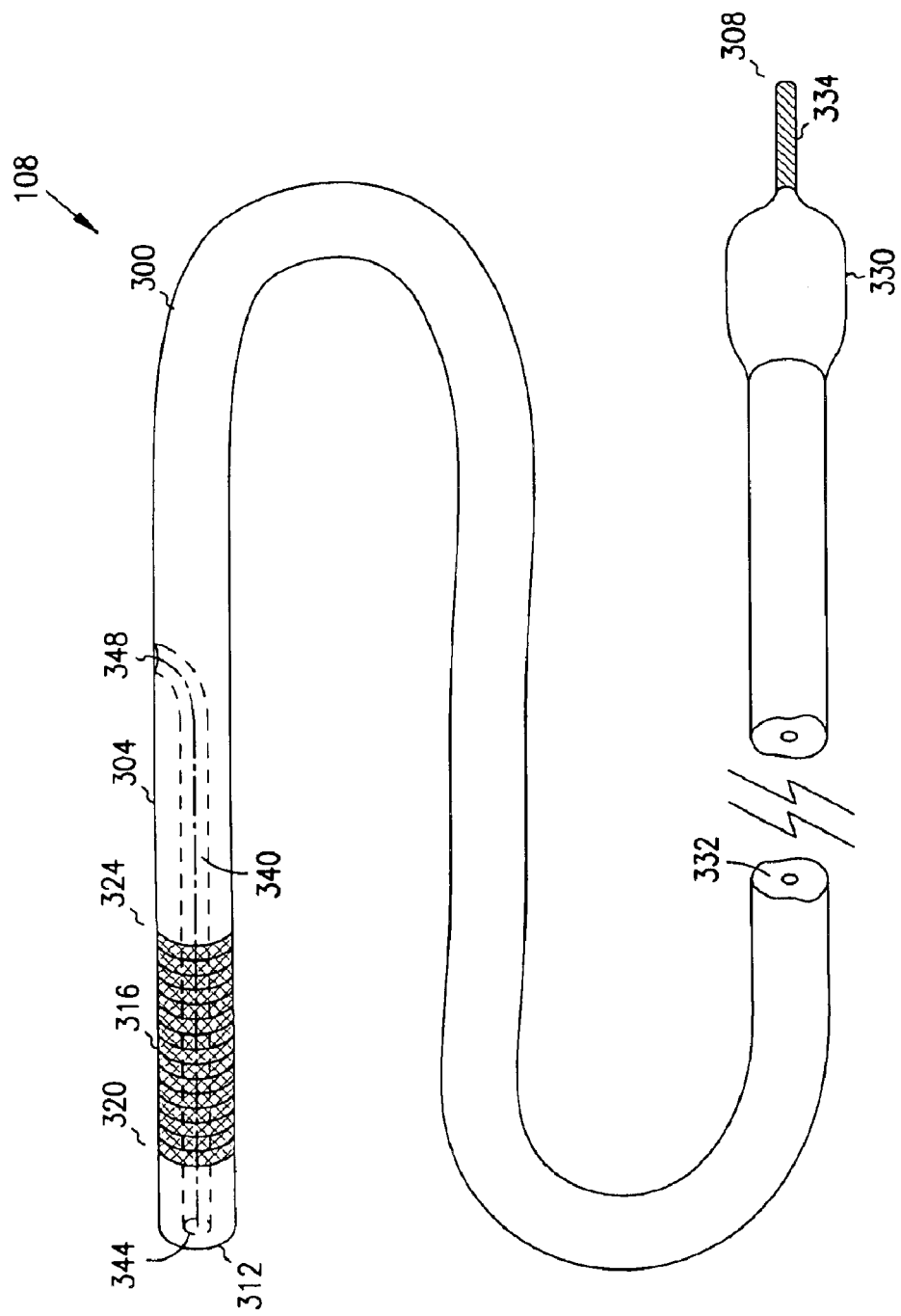
FIG. 3 is a schematic of a catheter according to one embodiment of the present subject matter.

Referring now to FIG. 3, there is shown one embodiment of the catheter 108 according to the present subject matter. The catheter 108 includes an elongate body 300 having a peripheral surface 304, proximal and distal ends 308 and 312. A first electrode 316 is attached on the peripheral surface 304 of the elongate body 300. In one embodiment, the first electrode 316 is a coil spring electrode which encircles the peripheral surface 304 of the elongate body 300, where the coil spring electrode has a first end 320 and a second end 324. The coil spring electrode provides the region adjacent the distal end 312 with flexibility while still providing a large electrical discharge surface area.

In one embodiment, the length of the first electrode 316 is selected to be between 80 and 120% of the length of an intravascular stent. In an alternative embodiment, the first electrode 316 has a length the range of 6 to 40 millimeters. In an additional embodiment, the length of the first electrode 316 is selected so that first electrode is positioned proximate the intravascular stent with the first electrode within the lumen of the intravascular stent where the first and second electrode ends are aligned with the first and second ends of the stent, respectively. Alternatively, the first electrodes 316 has a length that allows for the first electrode 316 to be positioned completely within the lumen of the stent, or to be positioned with both the first and second ends of the first electrode extending beyond the first and second ends of the stent.

In one embodiment, the first end 320 of the first electrode 316 is spaced longitudinally along the peripheral surface 304 from the distal end 312 by a distance in the range of 2 to 20 millimeters, where 10 millimeters is an acceptable distance. It is understood, however, that the first end 320 of the first electrode 316 can be located at any number of distances from the distal end 312, provided the first electrode 316 can still be positioned adjacent the intravascular stent. An electrical lead 332 extends longitudinally within the elongate body 300 from a lead connector 330 at the proximal end 308 to electrically connect to the first electrode 316.

The catheter 108 also includes a lead pin 334 electrically coupled to the electrical lead 332, where the lead pin 334 is provided at the lead connector 330. In one embodiment, the lead connector 330 is releasably attach to the pulse generator 140 through the first or second input/output socket 150 or 152, where lead pin 334 engages a connector terminal within the input/output socket 150 or 152 to electrically couple the first electrode to the pulse generator 140.

In one embodiment, the elongate body 300 of the catheter 108 is made of an extruded polyurethane biocompatible polymer. In an alternative embodiment, the elongate body 300 of the catheter 108 is made of an extruded silicon rubber. Alternatively, the elongate body 300 of the catheter 108 can be made of any implantable flexible biocompatible polymer (e.g., nylon or polyester) The length of the elongated body 300 of the catheter 108 between the proximal and distal ends 308 and 312 is in the range of 90 to 150 centimeters. Additionally, the diameter of the elongate body 300 is in the range of 1 to 3 millimeters (3 to 9 French). In one embodiment, the diameter of the elongate body 300 is less than the lumenal diameter of the deployed stent.

The electrically conductive lead 332 is constructed of either stainless steel, platinum, or alloys such as MP35N. The first electrode 316 is made of an implantable metal known in the art, such as platinum, titanium, titanium oxide, titanium nitride, carbon, tantalum pentoxide, iridium, or iridium oxide. Other materials suitable for conductor leads and electrodes are also known in the art and are considered to be within the scope of the present subject matter.

The catheter 108 has a guidewire passageway 340 extending longitudinally in the elongate body 300 from an inlet end 344 located at the distal end 312 to a outlet end 348 located along the peripheral surface 304 of the elongate body 300. In an alternative embodiment, the guidewire passageway 340 extends longitudinally in the elongate body 300 from the inlet end 344 to an outlet end located at the proximal end 308 of the elongate body 300. In one embodiment, the guidewire passageway 340 is adapted to receive a guidewire for guiding the catheter 108 over the guidewire positioned in the artery. In one embodiment, the guidewire lumen in approximately 20 thousandths of an inch in diameter.

The catheter 108 is relatively flexible at the tip in order to track over the guidewire thus allowing the catheter 108 to advance through patient's arteries. In addition, the catheter includes appropriate axial stiffness (or column strength) at the proximal end 308 to allow for appropriate pushability of the catheter. Choices of catheter design, materials and construction techniques are known which can improve the trackability and the pushability of a catheter intended to be inserted into the arteries. Furthermore, the coil structure of the first electrode 140 allows for improved flexibility and trackability of the catheter over the guidewire.

Figure 4:
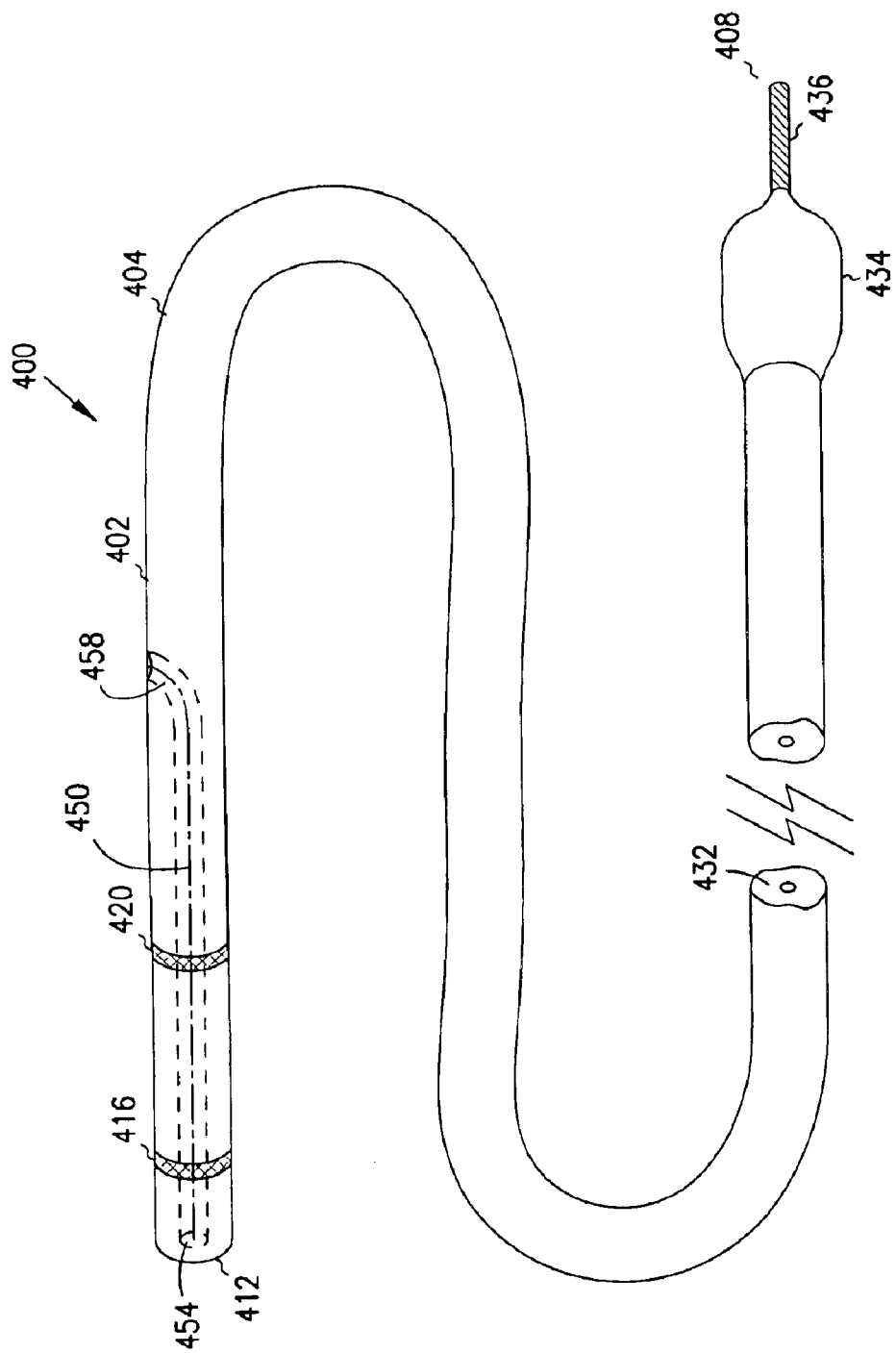
FIG. 4 is a schematic of a catheter according to one embodiment of the present subject matter.

Referring now to FIG. 4, there is shown an alternative embodiment of a catheter 400 according to the present subject matter. The catheter 400 includes an elongate body 402 having a peripheral surface 404, proximal and distal ends 408 and 412. A first electrode 416 and a third electrode 420 are attached on the peripheral surface 404 of the elongate body 402. In one embodiment, the first electrode 416 and the third electrode 420 are annular and encircle the peripheral surface 404 of the elongate body 402.

In one embodiment, the first electrode 416 and the third electrode 420 are spaced apart and spaced longitudinally along the peripheral surface 404 by a distance of between 80 to 120% the length of the intravascular stent. In an alternative embodiment, the first and third electrodes 416 and 420 are spread apart in the range of 6 to 40 millimeters. In addition, the first electrode 416 is spaced longitudinally along the peripheral surface 404 from the distal end 412 by a distance in the range of 2 to 20 millimeters. In one embodiment, the first and third electrodes 416 and 420 are spread apart so the first electrode 416 is positioned adjacent a first end of the stent and the third electrode 420 is positioned adjacent a second end of the stent. It is understood, however, that the first electrode 416 can be located at any number of distances from the distal end 412, provided the first electrode 416 and the third electrode 420 can be positioned adjacent the intravascular stent.

An electrical lead 432 extends longitudinally within the elongate body 404 from a lead connector 434 at the proximal end 408 to electrically connect the first electrode 416 and the third electrode 420 in common. In one embodiment, a lead pin 436 electrically coupled to the electrical lead 432 is provided at the lead connector 434 to allow the first electrode 416 and the third electrode 420 to be releasably attached and electrically coupled to the pulse generator 140 as previously discussed.

In one embodiment, the elongate body 402 of the catheter 400 is made of an extruded polyurethane biocompatible polymer. In an alternative embodiment, the elongate body 402 of the catheter 400 is made of an extruded silicon rubber biocompatible polymer. Alternatively, the elongate body 402 of the catheter 400 can be made of any implantable flexible biocompatible polymer. The length of the elongated body 402 of the catheter 400 between the proximal and distal ends 408 and 412 is in the range of 90 to 150 centimeters. Finally, the diameter of the catheter is in the range of 1 to 3 millimeters (3 to 9 French), where the diameter of the elongate body is small enough to allow the catheter 400 to pass through the lumen of the intravascular stent.

The electrically conductive lead 432 is constructed of either stainless steel, platinum, or MP35N. The first and third electrodes 416 and 420 are made of an implantable metal known in the art, such as platinum, titanium, titanium oxide, titanium nitride, carbon, tantalum pentoxide, iridium, or iridium oxide. Other materials suitable for conductor leads and electrodes are also known in the art and are considered to be within the scope of the present subject matter.

The catheter 400 has a guidewire passageway 450 extending longitudinally in the elongate body 404 from an inlet end 454 located at the distal end 412 to a outlet end 458 located along the peripheral surface 404 of the elongate body 402. In an alternative embodiment, the guidewire passageway 450 extends longitudinally in the elongate body 402 from the inlet end 454 to an outlet end located at the proximal end 408 of the elongate body 402. The guidewire passageway 454 is adapted to receive a guidewire for guiding the catheter 400 over the guidewire positioned in the arteries.

Additionally the catheter 400 is relatively flexible at the tip to track over the guidewire to allow the catheter 400 to advance through patient's arteries. In addition, the catheter 400 includes appropriate axial stiffness (or column strength)

at the proximal end 408 to allow for appropriate pushability of the catheter. Catheter design choices, materials and construction techniques are known which can improve the trackability and the pushability of a catheter intended to be inserted into the arteries.

In an alternative embodiment, the third electrode 420 is coupled to a third lead conductor housed within the elongate body 402. The third lead conductor is coupled to a lead pin positioned on the lead connector 434. The input/output socket is adapted to receive the lead connector 434 so that bipolar cardiac signals can be received and bipolar electrical energy can be provided to the first and third electrodes 416 and 420 from the pulse generator 140. In this present embodiment, electrocardiogram signals used in coordinating the production of electrical energy pulses (e.g., electrical or radio frequency) are sensed from two or more surface electrocardiogram electrodes, where each of the two or more surface electrocardiogram electrodes is coupled to a lead connector of two or more lead connectors which are connected to the pulse generator 140. In an alternative embodiment, unipolar signals and electrical energy can be produced and supplied across the electrodes by coupling the first and third electrodes in common within the pulse generator 140.

Figure 5:
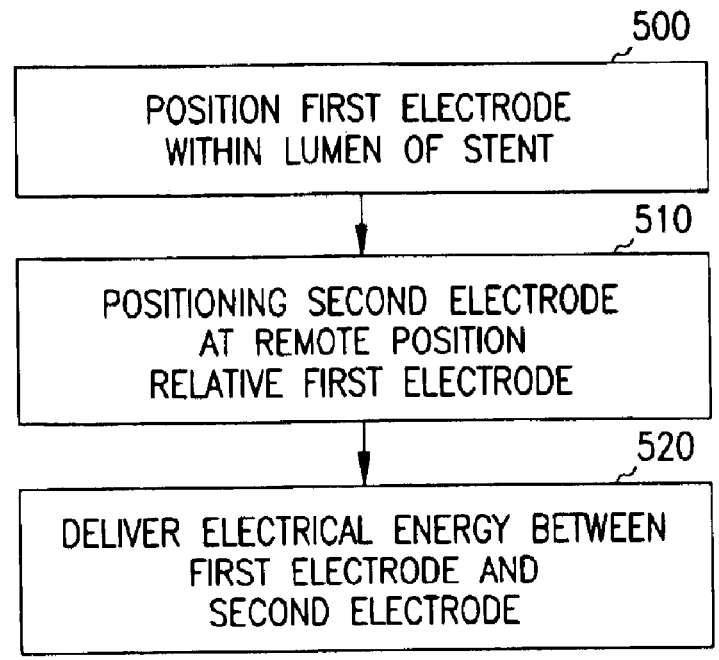
FIG. 5 is a flow chart illustrating one embodiment of the present subject matter.

Referring now to FIG. 5, there is shown a flow diagram of one embodiment of the present subject matter. At 500, at least a portion of a first electrode is positioned within a lumen of a stent. In one embodiment, the stent has been implanted within an artery, where the catheter is inserted into the vasculature to align the first and second electrode ends of the first electrode with the first and second stent ends of the stent. At 510, a second electrode is then positioned at a remote position relative to the first electrode. In one embodiment, the remote position is a portion of skin of the patient in which the first electrode has been positioned. At 520, electrical energy is then delivered between the first electrode and the second electrode.

Figure 6:
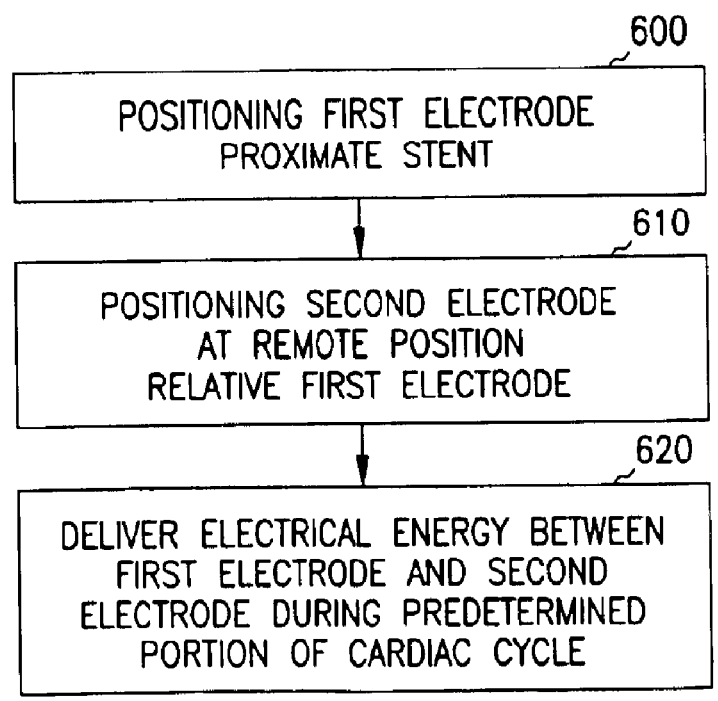
FIG. 6 is a flow chart illustrating one embodiment of the present subject matter.

Referring now to FIG. 6, there is shown a flow diagram of an additional embodiment of the present subject matter. At 600, after placing an intravascular stent in an artery, the catheter is inserted into the vasculature to position either the first electrode (FIG. 3) or the first and third electrodes (FIG. 4) in a location proximate the implanted stent. In one embodiment, the electrode is positioned concentrically within the lumen formed by the implanted stent. In one embodiment, the ends of the electrode (e.g., 320 and 324 of FIG. 3, or 416 and 420 of FIG. 4) are positioned adjacent to and aligned with the ends of the implanted stent. In an alternative embodiment, the electrode is positioned in a vein or artery that is adjacent to the stented artery. The second electrode is then positioned at a remote position relative to the first electrode at 610. In one embodiment, the remote position is approximately at the left lateral aspect of the thorax. In an alternative embodiment, the remote position is a dermal surface on the torso. The first and second, or the first, second and third, electrodes are then coupled to the pulse generator. Cardiac signals are then sensed, and electrical energy is delivered between the first electrode and the second electrode (or the first, second and third electrodes) during a predetermined portion of the cardiac cycle at 620.

Figure 7:
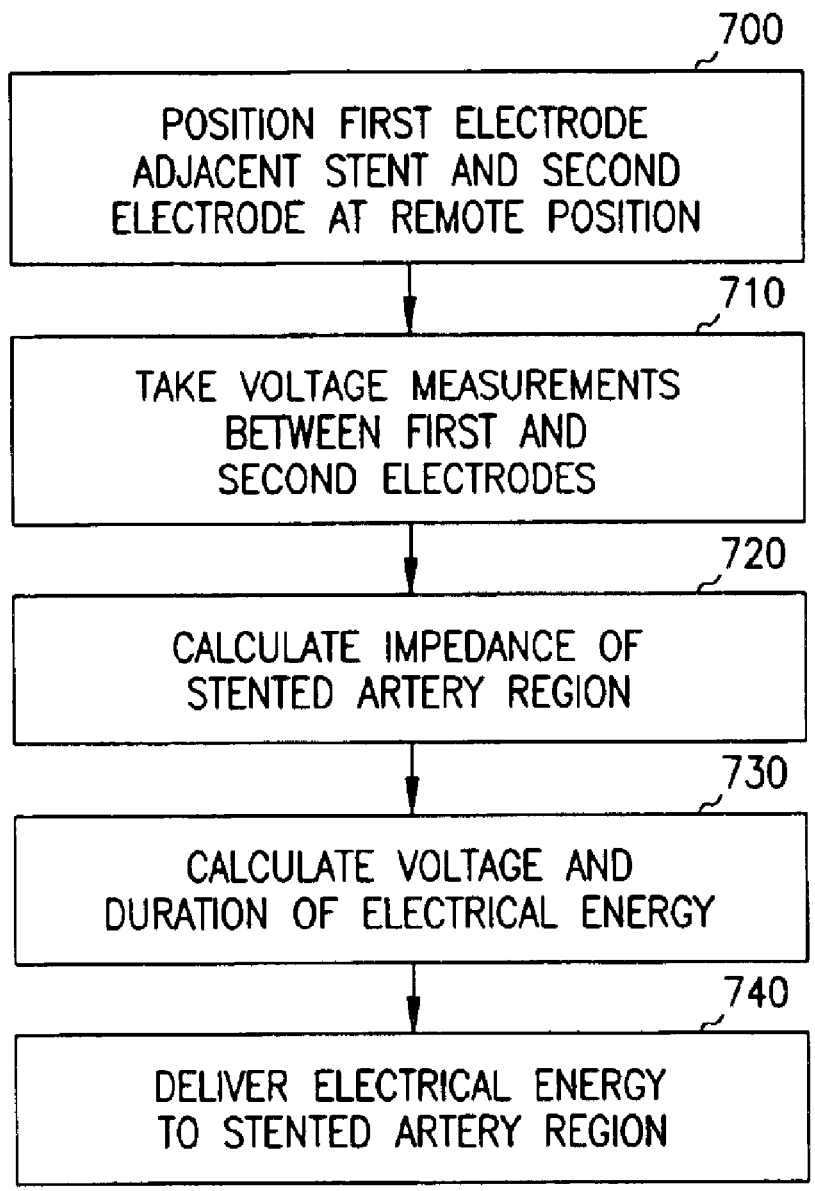
FIG. 7 is a flow chart illustrating one embodiment of the present subject matter.

Referring now to FIG. 7, there is shown a flow diagram of an additional embodiment of the present subject matter. At 700, the first electrode is positioned within an artery proximate an implanted stent. A second electrode, as previously described, is positioned at a remote position relative to the first electrode to allow for the electrical energy to be delivered between the first electrode and the second electrode.

At 710, voltage measurements are made for the electrical energy by taking bipolar impedance measurements across the first and second electrodes. To make these measurements, a constant low current shock is provided through the electrodes. In one embodiment, the constant low current shock is provided as direct current between the two electrodes. In an alternative embodiment, the current applied between the electrodes is a subthreshold alternating current. In one embodiment, the low current or subthreshold alternating current is delivered in the range of 10 to 50 microamperes. When an alternating current is used, the frequency of current pulses is delivered in the range of 5 to 50 KHz, where 20 KHz is an appropriate value.

A bipolar measurement of the resultant voltage is made using the first and second electrodes. Once the resultant voltage has been measured, the impedance of the stented arterial region is calculated at 720. In one embodiment, the impedance is determined by using Ohm's law (V=IR) where R is impedance. Once the impedance has been determined, the voltage of the electrical energy required to deliver a specific amount of current is calculated at 730. In one embodiment, the voltage is calculated by assuming a critical current density. The critical current density is the current density required to effect changes in the cells residing the in the arterial structure. In one embodiment, the critical current density is a predetermined value in the range of 1 to 4 amperes/cm$^2$. The measured impedance and the critical current density are then used to calculate the voltage of the electrical energy to be delivered across the electrodes.

In one embodiment, the current to the electrode needed to achieve the current density is computed by multiplying the current density by the surface area of the electrode. This is only an approximate calculation since the current density along the electrode will be non-uniform. In one embodiment, an empirically determined correction factor might also be included in the equation to assure the critical current density is achieved along the entire electrode or stented region. Once the current is determined, the voltage is calculated by multiplying current times the impedance. Alternatively, the voltage of the electrical energy to be delivered across the electrodes can be determined by delivering a small voltage shock across the electrodes and measuring the resulting current. Based on the resulting current and the current desired to be delivered to the stented region, a multiplication factor can be calculated by dividing the desired current by the resulting current. The voltage value of the small shock can then be multiplied by the multiplication factor to determine the voltage of the electrical energy necessary to deliver the desired current. For example, if electrical energy delivered at 1.0 volt results in 10 milliamps of current, and it is desired to deliver 5 amps of current, it would then be known that a pulse of electrical energy having a voltage value of 500 volts would be required.

Once the voltage of the electrical energy has been determined, the pulse generator is programmed to deliver the electrical pulses as previously described and the electrical energy is delivered to the stented arterial region under the control of the pulse generator as previously described at 740.

Besides delivering electrical energy pulses to the stented region of the artery, other types of energy can be delivered. For example, an external defibrillator can use an RLC circuit to store and discharge energy, rather than a capacitor storage and discharge energy. In an additional embodiment, a radio frequency generator could also be used to generate energy to be delivered to the stented region of an artery. In one embodiment, the radio frequency generator is similar to those known in the catheter ablation art.

In addition to the embodiment of delivering electrical energy to stented coronary arteries, the present subject matter can also be used to deliver electrical energy to stents positioned in peripheral arteries. The problem of restenosis is known to be associated with peripheral stents and the present subject matter can be used in treating the portions of the peripheral vasculature in which a stent has been placed. Portions of the peripheral vasculature in which stents have been placed include the legs and the necks of patients. Therefore, the present subject matter is not limited to treatment of coronary arteries, but rather can include all regions of the vasculature in which a stent might be placed in order to support the structure of the vessel.

Figure 8:
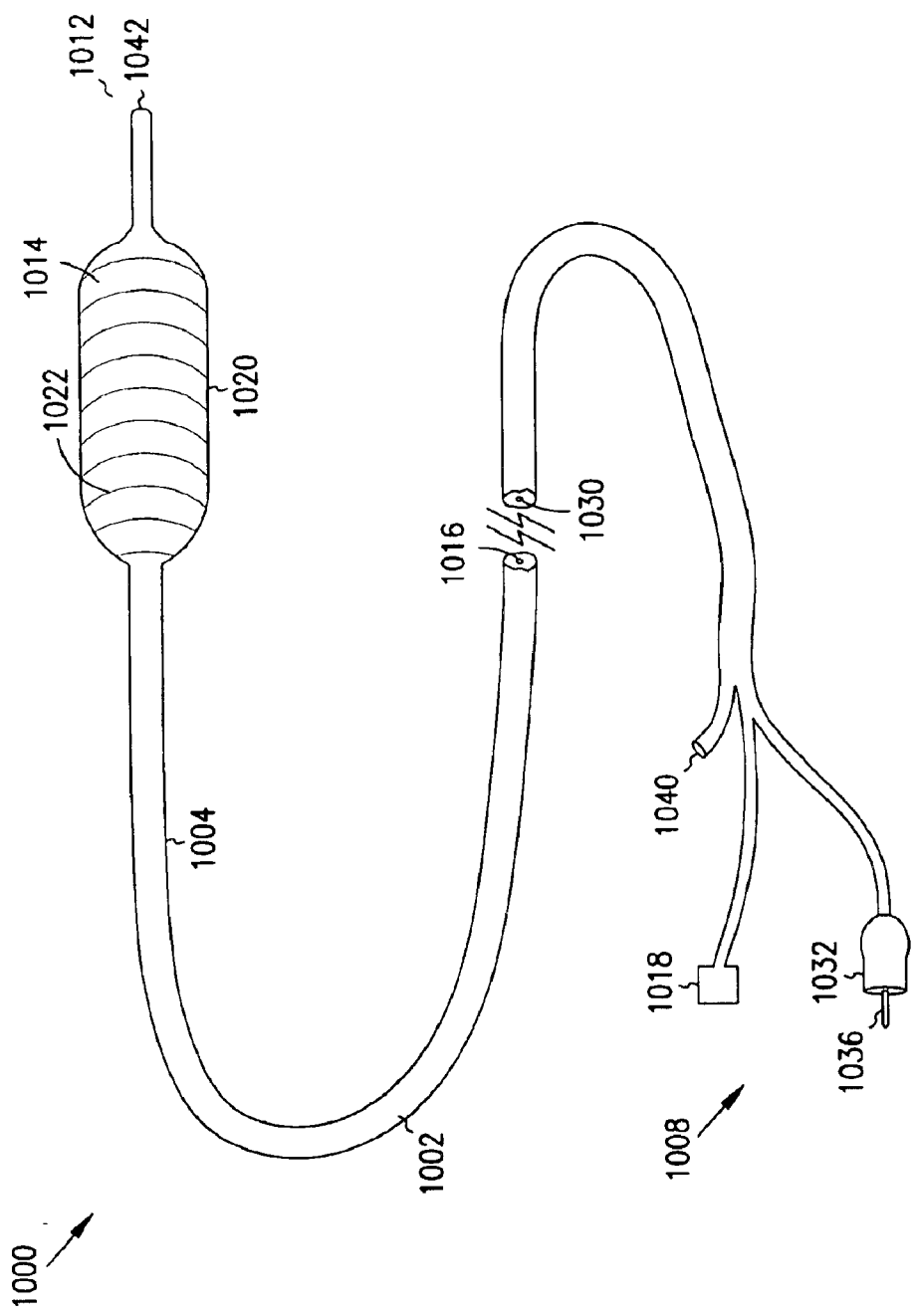
FIG. 8 is a schematic of a catheter according to one embodiment of the present subject matter.

Referring now to FIG. 8, there is shown an alternative embodiment of a catheter 1000 according to the present subject matter. The catheter 1000 includes an elongate body 1002 having a peripheral surface 1004, a proximal end 1008 and a distal end 1012. The catheter 1000 further includes an angioplasty balloon 1014 (shown in its expanded state) positioned proximal the distal end 1012 of the catheter 1000. The elongate body 1002 includes a lumen 1016 extending from an inlet port 1018 positioned at the proximal end 1008 to an outlet end (not shown) which opens into the interior region of the angioplasty balloon 1014. The inlet and outlet ports are designed to allow fluid to pass under pressure between the inlet and the outlet port for the purpose of expanding and contracting the angioplasty balloon 1014. Structures and procedures for creating and using catheters having angioplasty balloons are known.

The angioplasty balloon 1014 further includes a peripheral surface 1020. A first electrode 1022 is positioned on the peripheral surface 1020 of the angioplasty balloon 1014. In one embodiment, the first electrode 1022 is a flexible conductive layer which is coated onto the peripheral surface 1020 of the balloon 1014. In an alternative embodiment, the first electrode 1022 is a matrix of flexible conductive wires which are integrated into the peripheral surface 1020 of the balloon 1014, where portions of the wire surfaces are exposed at the peripheral surface 1020. The first electrode is coupled to an electrical lead 1030 which extends longitudinally within the elongate body 1002 from a lead connector 1032 at the proximal end 1008 to electrically connect to the first electrode 1022. In one embodiment, a lead pin 1036 electrically coupled to the electrical lead 1030 is provided at the lead connector 1032 to allow the first electrode 1022 to be releasably attached and electrically coupled to the pulse generator 140 as previously discussed.

In one embodiment, the catheter 1000 has a stent in its unexpanded state positioned over the balloon 1014. The stent and the balloon are advanced over the guidewire to position the stent in the lumen of an artery to be dilated. The balloon is then inflated. Inflating the balloon 1014 causes the structure of the stent to expand radially to contact and engage the interior surface of the artery. As the balloon is in its inflated position, the first electrode 1022 is in physical contact with the stent. When the stent and the first electrode 1022 are in contact, the pulse generator (as previously described) can be used to generate pulses of electrical energy. In one embodiment, this electrical energy is delivered between the first electrode 1022 and the second electrode, as previously described.

In one embodiment, the first electrode 1022 has a length of between 80 to 120% the length of the intravascular stent. In an alternative embodiment, the first electrode 1022 has a length in the range of 6 to 40 millimeters. In one embodiment, the elongate body 1002 of the catheter 1000 is made of an extruded polyurethane biocompatible polymer. Alternatively, the elongate body 1002 is made from either an extruded nylon or polyester. In addition, the length of the elongated body 1002 between the proximal and distal ends 1008 and 1012 is in the range of 90 to 150 centimeters. Finally, the diameter of the catheter with the angioplasty balloon uninflated is in the range of 1 to 3 millimeters (3 to 9 French).

The electrically conductive lead 1032 is constructed of either stainless steel, platinum, or MP35N. The first electrodes 1022 is made of an implantable metal known in the art, such as platinum, titanium, titanium oxide, titanium nitride, carbon, tantalum pentoxide, iridium, or iridium oxide. Other materials suitable for conductor leads and electrodes are also known in the art and are considered to be within the scope of the present subject matter.

The catheter 1000 further includes a guidewire passageway (not shown) extending longitudinally in the elongate body 1002 from an inlet end 1040 located at the proximal end 1008 to a outlet end 1042 located at the distal end 1012 of the elongate body 1002. In an alternative embodiment, the guidewire passageway extends longitudinally through a portion of the elongate body 1002 from the inlet end located along the peripheral surface 1004 of the elongate body 1002 to the outlet end located 1042 at the distal end 1012 of the elongate body 1002. The guidewire passageway is adapted to receive a guidewire for guiding the catheter 1000 over the guidewire positioned in the arteries.

Additionally the catheter 1000 is relatively flexible at the tip to track over the guidewire to allow the catheter 1000 to advance through patient's arteries. In addition, the catheter 1000 includes appropriate axial stiffness (or column strength) at the proximal end 1008 to allow for appropriate pushability of the catheter. Catheter design choices, materials and construction techniques are known which can improve the trackability and the pushability of a catheter intended to be inserted into the arteries.

The present subject matter has now been described with reference to several embodiments thereof. It will be apparent to those skilled in the art that may changes and modifications can be made to the embodiments described without departing from the scope of the present invention. For example, radioopaque markers can be added to the body of the catheter to assist the physician in positioning the electrode adjacent to a stent implanted in a arterial artery.

We claim:

1. A method comprising:
    positioning a first electrode near an implanted intravascular stent;
    positioning a second electrode at a different position from the first electrode; and
    delivering at least one pulse of electrical energy between the first and second electrodes at a repetition rate that is less than or equal to the order of a frequency between heart depolarizations.

2. The method of claim 1, wherein the positioning the second electrode includes positioning the second electrode at a remote position outside a lumen of the stent.

3. The method of claim 2, wherein the positioning the second electrode includes positioning the second electrode external to a patient.

4. The method of claim 3, wherein the positioning the second electrode includes positioning the second electrode on a dermal surface.

5. The method of claim 1, wherein the positioning the first electrode includes positioning the first electrode within a blood vessel.

6. The method of claim 5, wherein the positioning the first electrode includes positioning at least a portion of the first electrode within a lumen of stent.

7. The method of claim 5, wherein the positioning the first electrode includes positioning the first electrode within a lumen of the stent such that first and second electrode ends substantially align with respective first and second stent ends.

8. The method of claim 1, wherein positioning the first electrode includes positioning the first electrode on a catheter, and wherein the positioning the second electrode includes positioning the second electrode on the same catheter.

9. The method of claim 1, wherein at least one of the positioning the first electrode and the positioning the second electrode includes contacting one of the first and second electrodes with the stent.

10. The method of claim 1, further including sensing a cardiac signal, and wherein the delivering at least one pulse includes delivering the at least one pulse during a predetermined portion of a cardiac cycle.

11. The method of claim 1, in which the delivering at least one pulse includes discharging a capacitor.

12. The method of claim 1, in which the delivering at least one pulse includes delivering at least one substantially constant current pulse.

13. The method of claim 1, in which the delivering at least one pulse includes delivering at least one substantially direct current (DC) pulse.

14. The method of claim 1, in which the delivering at least one pulse includes delivering at least one pulse having a current density between about 1 ampere/cm$^2$ and about 4 amperes/cm$^2$.

15. The method of claim 1, in which the positioning the first electrode includes contacting the first electrode with the stent.

16. A method comprising:
positioning a first electrode near an implanted intravascular stent;
positioning a second electrode at a different position from the first electrode;
measuring an impedance between the first and second electrodes;
determining a desired energy level, using the measured impedance, for inhibiting or reducing stenosis; and
delivering electrical energy at the desired energy level between the first electrode and the second electrode to inhibit or reduce stenosis.

17. The method of claim 16, wherein the positioning the second electrode includes positioning the second electrode at a remote position outside a lumen of the stent.

18. The method of claim 17, wherein the positioning the second electrode includes positioning the second electrode external to a patient.

19. The method of claim 18, wherein the positioning the second electrode includes positioning the second electrode on a dermal surface.

20. The method of claim 16, wherein the positioning the first electrode includes positioning the first electrode within a blood vessel.

21. The method of claim 20, wherein the positioning the first electrode includes positioning at least a portion of the first electrode within a lumen of stent.

22. The method of claim 20, wherein the positioning the first electrode includes positioning the first electrode within a lumen of the stent such that first and second electrode ends substantially align with respective first and second stent ends.

23. The method of claim 16, wherein positioning the first electrode includes positioning the first electrode on a catheter, and wherein the positioning the second electrode includes positioning the second electrode on the same catheter.

24. The method of claim 16, wherein at least one of the positioning the first electrode and the positioning the second electrode includes contacting one of the first and second electrodes with the stent.

25. The method of claim 16, further including sensing a cardiac signal, and wherein the delivering electrical energy includes delivering at least one pulse during a predetermined portion of a cardiac cycle.

26. The method of claim 16, in which the delivering electrical energy includes discharging a capacitor.

27. The method of claim 16, in which the delivering electrical energy includes delivering at least one substantially constant current pulse.

28. The method of claim 16, in which the delivering electrical energy includes delivering at least one substantially direct current (DC) pulse.

29. The method of claim 16, in which the delivering electrical energy includes delivering at least one pulse having a current density between about 1 ampere/cm$^2$ and about 4 amperes/cm$^2$.

30. The method of claim 16, in which the positioning the first electrode includes contacting the first electrode with the stent.

31. A method comprising:
positioning a first electrode near an implanted intravascular stent;
positioning a second electrode at a different position from the first electrode;
measuring an impedance between the first and second electrodes;
determining a desired energy level, using the measured impedance, wherein the desired energy level is appropriate for inhibiting or reducing stenosis without affecting nearby myocardial tissue;
delivering electrical energy at the desired energy level between the first and second electrodes.

32. The method of claim 31, wherein the positioning the second electrode includes positioning the second electrode at a remote position outside a lumen of the stent.

33. The method of claim 32, wherein the positioning the second electrode includes positioning the second electrode external to a patient.

34. The method of claim 33, wherein the positioning the second electrode includes positioning the second electrode on a dermal surface.

35. The method of claim 31, wherein the positioning the first electrode includes positioning the first electrode within a blood vessel.

36. The method of claim 35, wherein the positioning the first electrode includes positioning at least a portion of the first electrode within a lumen of stent.

37. The method of claim 35, wherein the positioning the first electrode includes positioning the first electrode within a lumen of the stent such that first and second electrode ends substantially align with respective first and second stent ends.

38. The method of claim 31, wherein positioning the first electrode includes positioning the first electrode on a catheter, and wherein the positioning the second electrode includes positioning the second electrode on the same catheter.

39. The method of claim 31, wherein at least one of the positioning the first electrode and the positioning the second electrode includes contacting one of the first and second electrodes with the stent.

40. The method of claim 31, further including sensing a cardiac signal, and wherein the delivering electrical energy includes delivering at least one pulse during a predetermined portion of a cardiac cycle.

41. The method of claim 31, in which the delivering electrical energy includes discharging a capacitor.

42. The method of claim 31, in which the delivering electrical energy includes delivering at least one substantially constant current pulse.

43. The method of claim 31, in which the delivering electrical energy includes delivering at least one substantially direct current (DC) pulse.

44. The method of claim 31, in which the delivering electrical energy includes delivering at least one pulse having a current density between about 1 ampere/cm$^2$ and about 4 amperes/cm$^2$.

45. The method of claim 31, in which the measuring the impedance includes:
delivering a test current between the first and second; and
measuring a resulting voltage between the first and second electrodes, the resulting voltage resulting from the delivering the test current.

46. The method of claim 31, in which the determining the desired energy level of the electrical energy includes determining a voltage amplitude of the electrical energy.

47. The method of claim 46, in which the determining the voltage amplitude of the electrical energy includes calculating the voltage amplitude using the measured impedance and a predetermined critical current density value.

48. The method of claim 47, in which the calculating the voltage amplitude includes multiplying the predetermined critical current density value by a surface area of at least one of the first and second electrodes.

49. The method of claim 31, in which the positioning the first electrode includes contacting the first electrode with the stent.

50. A method comprising:
positioning a first electrode near an implanted intravascular stent;
positioning a second electrode at a different position from the first electrode;
measuring an impedance using the first and second electrodes;
determining a desired energy level, using the measured impedance, in which the desired energy level is determined using a predetermined desired current density between the first and second electrodes; and
delivering electrical energy between the first and second electrodes at the desired energy level to inhibit or reduce stenosis.

51. The method of claim 50, wherein the positioning the second electrode includes positioning the second electrode at a remote position outside a lumen of the stent.

52. The method of claim 51, wherein the positioning the second electrode includes positioning the second electrode external to a patient.

53. The method of claim 52, wherein the positioning the second electrode includes positioning the second electrode on a dermal surface.

54. The method of claim 50, wherein the positioning the first electrode includes positioning the first electrode within a blood vessel.

55. The method of claim 54, wherein the positioning the first electrode includes positioning at least a portion of the first electrode within a lumen of stent.

56. The method of claim 54, wherein the positioning the first electrode includes positioning the first electrode within a lumen of the stent such that first and second electrode ends substantially align with respective first and second stent ends.

57. The method of claim 55, wherein positioning the first electrode includes positioning the first electrode on a catheter, and wherein the positioning the second electrode includes positioning the second electrode on the same catheter.

58. The method of claim 50, wherein at least one of the positioning the first electrode and the positioning the second electrode includes contacting one of the first and second electrodes with the stent.

59. A method comprising:
positioning a first electrode near an implanted intravascular stent;
positioning a second electrode at a different position from the first electrode; and
delivering a substantially constant DC current between the first electrode and the second electrode;
measuring an impedance using the substantially constant DC current;
determining a desired energy level, using the measured impedance, for inhibiting or reducing stenosis; and
delivering electrical energy between the first and second electrodes at the desired energy level to inhibit or reduce stenosis.

60. The method of claim 59, wherein the positioning the second electrode includes positioning the second electrode at a remote position outside a lumen of the stent.

61. The method of claim 59, wherein the positioning the second electrode includes positioning the second electrode external to a patient.

62. The method of claim 61, wherein the positioning the second electrode includes positioning the second electrode on a dermal surface.

63. The method of claim 59, wherein the positioning the first electrode includes positioning the first electrode within a blood vessel.

64. The method of claim 63, wherein the positioning the first electrode includes positioning at least a portion of the first electrode within a lumen of stent.

65. The method of claim 63, wherein the positioning the first electrode includes positioning the first electrode within a lumen of the stent such that first and second electrode ends substantially align with respective first and second stent ends.

66. The method of claim 59, wherein positioning the first electrode includes positioning the first electrode on a catheter, and wherein the positioning the second electrode includes positioning the second electrode on the same catheter.

67. The method of claim 59, wherein at least one of the positioning the first electrode and the positioning the second electrode includes contacting one of the first and second electrodes with the stent.

68. The method of claim 59, in which the positioning the first electrode includes contacting the first electrode with the stent.

69. The method of claim 16, in which the determining the desired energy level includes establishing the desired energy at a level that is sufficient to inhibit or reduce stenosis without impairing nearby myocardial cells.

70. The method of claim 16, in which the determining the desired energy level includes establishing the desired energy at an energy that is sufficient to affect smooth muscle cells in a medial layer of a blood vessel without impairing nearby myocardial cells.

71. The method of claim 16, in which the measuring the impedance includes delivering a test current, measuring a resulting voltage, and calculating the impedance using the test current and the measured resulting voltage.

72. The method of claim 71, in which the delivering the test current includes delivering a subthreshold alternating current.

73. The method of claim 72, in which the delivering the subthreshold alternating current includes delivering the subthreshold alternating current at a frequency between about 5 kiloHertz and about 50 kiloHertz.

74. The method of claim 71, in which the delivering the test current includes delivering a test current having an amplitude between about 10 microamperes and about 50 microamperes.

75. The method of claim 16, in which the positioning the first electrode includes positioning an electrode on a balloon portion of a catheter.

76. The method of claim 16, in which the positioning the first electrode includes positioning a coil spring electrode.

* * * * *

UNITED STATES PATENT AND TRADEMARK OFFICE
CERTIFICATE OF CORRECTION

PATENT NO. : 6,939,345 B2
DATED : September 6, 2005
INVENTOR(S) : Ken Knight et al.

It is certified that error appears in the above-identified patent and that said Letters Patent is hereby corrected as shown below:

Title page,
Item [56], References Cited, OTHER PUBLICATIONS,
"Burns, Brent E.," reference, insert -- , -- before "1984".
"Carr, William N.," reference, insert -- ( -- before "Jun.".

Column 17,
Line 23, after "second" insert -- electrodes --.

Column 18,
Line 8, delete "claim 55" and insert -- claim 50 --.

Signed and Sealed this

Tenth Day of January, 2006

JON W. DUDAS
*Director of the United States Patent and Trademark Office*